(12) United States Patent
Musa et al.

(10) Patent No.: US 7,528,404 B2
(45) Date of Patent: May 5, 2009

(54) ASSEMBLY OF A SEMICONDUCTOR DIE ATTACHED TO SUBSTRATE WITH OXAZOLINE DERIVATIVE BEARING AN ELECTRON DONOR OR ACCEPTOR FUNCTIONALITY

(75) Inventors: Osama M. Musa, Hillsborough, NJ (US); Ruzhi Zhang, Pennington, NJ (US)

(73) Assignee: Henkel AG & Co. KGaA, Düsseldorf (DE)

( * ) Notice: Subject to any disclaimer, the term of this patent is extended or adjusted under 35 U.S.C. 154(b) by 362 days.

(21) Appl. No.: 10/555,291

(22) PCT Filed: Feb. 17, 2004

(86) PCT No.: PCT/US2004/004736

§ 371 (c)(1),
(2), (4) Date: Nov. 2, 2005

(87) PCT Pub. No.: WO2005/083771

PCT Pub. Date: Sep. 9, 2005

(65) Prior Publication Data

US 2006/0263928 A1      Nov. 23, 2006

(51) Int. Cl.
*H01L 29/08* (2006.01)
*H01L 35/24* (2006.01)
*H01L 51/00* (2006.01)
(52) U.S. Cl. ........................................ 257/40
(58) Field of Classification Search .................... 257/40
See application file for complete search history.

(56) References Cited

U.S. PATENT DOCUMENTS

| 5,356,947 | A | 10/1994 | Ali et al. |
| 5,439,978 | A | 8/1995 | Parkinson et al. |
| 6,372,859 | B1 * | 4/2002 | Sakata et al. ................ 525/432 |
| 2003/0208016 | A1 * | 11/2003 | Dershem et al. ............. 526/262 |
| 2004/0034142 | A1 * | 2/2004 | Kawakami et al. .......... 524/417 |
| 2005/0008832 | A1 * | 1/2005 | Santos et al. ................ 428/209 |

FOREIGN PATENT DOCUMENTS

EP            0222165         5/1987

OTHER PUBLICATIONS

Nakahama, Sejichi et al.: "Anionic Living Polymerization of Styrenes Containing Electron-withdrawing Groups"; Makromol. Chem., Macromol. Symp. 67, 223-236 (1993).

* cited by examiner

*Primary Examiner*—Jerome Jackson
*Assistant Examiner*—Anthony Ho
(74) *Attorney, Agent, or Firm*—Jane E. Gennaro

(57) ABSTRACT

An assembly of a semiconductor die attached to a substrate is made with a composition comprising compounds that contain an oxazoline functionality and an electron acceptor or an electron donor functionality. Electron donor functionalities include styrenic, cinnamyl, and vinyl ether groups. Electron acceptor functionalities include maleimide, acrylate, fumarate, and maleate groups. An exemplary compound has the structure: formula (I).

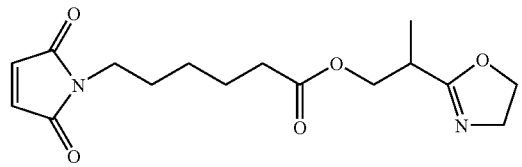

1 Claim, No Drawings

ASSEMBLY OF A SEMICONDUCTOR DIE ATTACHED TO SUBSTRATE WITH OXAZOLINE DERIVATIVE BEARING AN ELECTRON DONOR OR ACCEPTOR FUNCTIONALITY

FIELD OF THE INVENTION

This invention relates to an assembly of a semiconductor die attached to a substrate with a curable or cured composition that contains a compound having both oxazoline functionality and electron acceptor or electron donor functionality.

BACKGROUND OF THE INVENTION

The fabrication of semiconductor packages and microelectronic devices call for the use of adhesive and encapsulant compositions in assembly processes. Typical compositions include radical-curable compositions and electron donor/electron acceptor systems. These do not always give optimum performance in certain uses and there is still a need for performance materials within the semiconductor fabrication industry.

SUMMARY OF THE INVENTION

This invention is directed to an assembly of a semiconductor die attached to or supported on a substrate with a composition comprising a compound that contains an oxazoline functionality and an electron acceptor or an electron donor functionality. The composition is applied in a curable state and cured in situ. Electron donor functionalities include styrenic, cinnamyl, and vinyl ether groups. Electron acceptor functionalities include maleimide, acrylate, fumarate, and maleate groups.

DETAILED DESCRIPTION OF THE INVENTION

Oxazolines are five-membered heterocyclic compounds having a nitrogen atom, an oxygen atom, and one double bond. The double bond may be located in one of the three positions, making possible the existence of three different oxazoline rings: 2-oxazolines (most common), 3-oxazolines, and 4-oxazolines. Oxazolines undergo cationic ring opening homopolymerization; electron donor/electron acceptor systems undergo free radical polymerization. Thus, compounds having at least one oxazoline group and one electron donor or electron acceptor functionality per molecule have the capability of undergoing dual cure, both thermal and radiation.

The compositions used herein comprise a compound having oxazoline and electron donor or electron acceptor functionalities, curing agent and filler. In those compositions in which an electron acceptor functionality is present, the curing agent is optional. The composition can be a paste, prepared by blending or milling, or can be a film, prepared by standard film making techniques known to those skilled in the art.

The composition will consist mainly of the compound having oxazoline and electron donor or electron acceptor functionalities; alternatively, the compound having oxazoline and electron donor or electron acceptor functonalities can be used in a lesser amount as an adhesion promoter to one or more other curable resins. When used as an adhesion promoter, the amount used in the composition will be an effective amount and will range from 0.005 to 20.0 percent by weight of the formulation.

When used as an adhesion promoter, the main component will be any other suitable curable resin, including, for example, epoxy, vinyl ether, thiolene, a resin derived from cinnamyl and styrenic starting compounds, fumarate, maleate, acrylate, maleimide, cyanate ester, oxetane, phenol, amino resin, propargyl ether, benzocyclobutene, and benzoxazine.

Suitable curing agents are thermal initiators and photoinitiators present in an effective amount to cure the composition. In general, those amounts will range from 0.1% to 30%, preferably 1% to 20%, by weight of the total organic material (that is, excluding any inorganic fillers) in the composition.

Preferred radical initiators include peroxides, such as butyl peroctoates and dicumyl peroxide, and azo compounds, such as 2,2'-azobis(2-methyl-propanenitrile) and 2,2'-azobis(2-methyl-butanenitrile). Preferred cabonic initiators include iodonium, oxonium, sulfonium, sulfoxonium, and various other onium salts. Other suitable cationic initiators include Lewis acid catalysts and alkylation agents, such as, arlysulfonate esters, e.g., methyl-p-toluenesuffonate and methyl trifluoromethanesulfonate. A preferred series of photoinitiators are those sold under the trademark Irgacure or Rhodorsil 2074 by Ciba Specialty Chemicals. In some formulations, both thermal initiation and photoinitiation may be desirable: the curing process can be started either by irradiation, followed by heat, or can be started by heat, followed by irradiation.

The curable compositions will cure within a temperature range of 60° C. to 250° C., and curing will be effected within a range of three seconds to three hours. The actual cure profile will vary with the components and can be determined without undue experimentation by the practitioner.

Suitable fillers can be conductive or nonconductive. Exemplary conductive fillers are carbon black, graphite, gold, silver, copper, platinum, palladium, nickel, aluminum, silicon carbide, boron nitride, diamond, and alumina. Exemplary nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoro-ethylene, vinylidene fluoride, vinyl fluoride, vinylidene chloride, and vinyl chloride. Fillers generally will be present in amounts of 20% to 90% by weight of the formulation.

These compositions are useful for attaching semiconductor dies to substrates or for supporting a semiconductor die as an underfill between the die and substrate. Typical substrates are fabricated from metal, for example, copper, silver, gold, nickel, alloys (such as, 42Fe/58Ni alloy), silver-coated copper, or palladium-coated copper; from organic material, for example, polyimides, polyamides, or polyesters; from ceramic; and from composites or laminates (such as, printed wire boards).

In a typical die attach operation, the adhesive in paste or film form is placed onto the substrate, such as the center paddle of the leadframe, and the silicon die contacted to the adhesive with heat and pressure. The exact process and processing parameters may vary from operation to operation. These parameters and processes are known to those skilled in the art and are not meant to form a part of this invention.

In a typical underfill operation, connections are made between electrical terminals on the die and corresponding electrical terminals on the substrate using metallic or polymeric solder. A bump of solder is placed on the terminals of the substrate, the terminals are aligned and contacted, and the resulting assembly heated to reflow the solder. A gap is created between the die and the substrate, which is filled with a polymeric encapsulant or underfill to reinforce the interconnect. There are variations in the processes for the underfill, for example, the underfill encapsulation may take place after the reflow of the solder or simultaneously with the reflow of the solder. These processes are known to those skilled in the art and are not meant to form a part of this invention.

The gist of this invention is the use of the oxazoline compounds as a die attach or underfill encapsulant for attaching or suppporting semiconductor dies to substrates.

Various synthetic routes to the oxazoline compounds can be devised with reference to the following synthetic schemes. To prepare a compound having both styrenic and oxazoline functionality such as

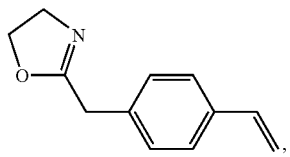

a procedure according to A. Zerroukhi, A. Ainser, A. Arsac, N. Mignard, and B. Marculescu, *Polymer Bulletin,* 42, 535, 1999, is used. Initially, vinylbenzyl chloride is reacted with sodium cyanide to give vinylbenzyl cyanide, which is then reacted with ethanolamine to give the vinylbenzyloxazoline.

To prepare a compound having both maleimide and oxazoline functionality such as

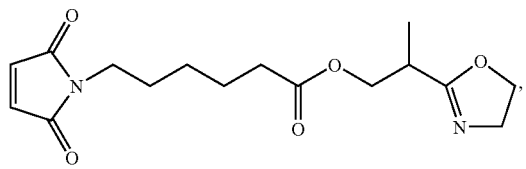

maleic anhydride (in acetonitrile) is reacted with 6-aminocaprioc acid (in acetic acid) to form the amic acid adduct. The adduct is dehydrated to close the ring and form the maleimide. Procedures for this reaction are known in the art. The product, 6-maleimidocaproic acid, is then reacted with 2-(3-hydroxy-2-propyl) -2-oxazoline (in toluene heated to 80° C.) with a catalytic amount of sulfuric acid, worked up, and the product isolated.

To prepare a compound having both cinnamyl and oxazoline functionality such as

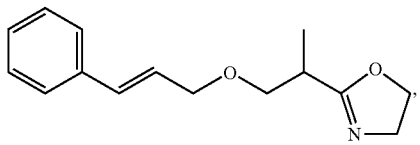

2-(3-hydroxy-2-propyl)-2-oxazoline in an excess amount of 50% NaOH and a catalytic amount of tetrabutyl ammonium hydrogen sulfate is reacted with cinnamyl chloride in toluene for several hours first at 53° C., then at 75° C. The reaction is allowed to cool to room temperature and the organic layer extracted and washed with brine three times. The isolated organic layer is dried over $MgSO_4$, filtered and the solvent removed in vacuo to give the product.

To prepare a compound having both styrenic and oxazoline functionality such as

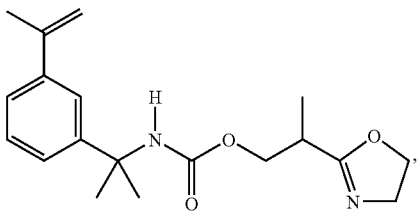

3-isopropenyl-α,α-dimethylbenzyl isocyanate (m-TMI) and 2-(3-hydroxy-2-propyl)-2-oxazoline are solvated in toluene and reacted under nitrogen with a catalytic amount of dibutyltin dilaurate at 60° C. for several hours. After the reaction is allowed to cool to room temperature, the solvent is removed in vacuo to give the product.

To prepare a compound having both acrylate and oxazoline functionality such as

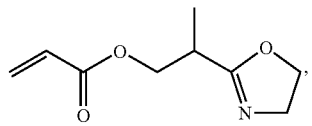

2-(3-hydroxy-2-propyl)-2-oxazoline and triethylamine are mixed in dry methylene chloride at 0° C. The appropriate equivalent of acryloyl chloride dissolved in dry methylene chloride is carefully added and the mixture allowed to react for several hours. The solvent is evaporated and the crude product is purified by column chromatography using a gradient of hexane/ethyl acetate.

To prepare a compound having both vinyl ether and oxazoline functionality such as

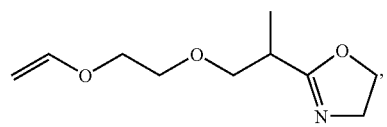

2-(3-hydroxy-2-propyl)-2-oxazoline in an excess amount of 50% NaOH and a catalytic amount of tetrabutyl ammonium hydrogen sulfate is reacted with 2-chloroethyl vinyl ether in toluene for several hours, first at 53° C., then at 75° C. The reaction is allowed to cool to room temperature and the organic layer extracted and washed with brine three times. The isolated organic layer is dried over $MgSO_4$, filtered, and the solvent removed in vacuo to give the product.

To prepare a compound having both maleate and oxazoline functionality such as

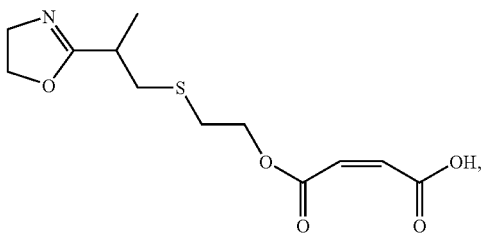

2-isopropenyl-2-oxazoline and 2-mercaptoethanol are reacted in toluene at 70° C. A solution of azodiisobutyronitrile (AIBN) in toluene is added to the mixture, and the reaction continued at 70° C. for several hours. The 2-isopropenyl-2-oxazoline/2-mercaptoethanol adduct is obtained after removal of the solvent under reduced pressure. This 2-isopropenyl-2-oxazoline/2-mercaptoethanol adduct is then reacted under nitrogen with maleic anhydride in 300 mL of dimethoxyethane at 70° C. for one hour. After cooling, the contents of the reaction are poured into heptane. The resulting product is dried at 40° C. in vacuo for 24 hours.

What is claimed is:

1. An assembly of a semiconductor die attached to a substrate with a composition consisting essentially of a compound having the structure,

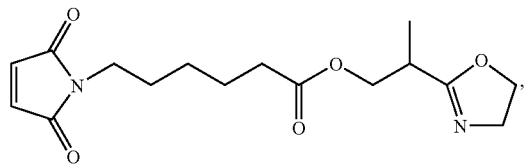

a curing agent and a filler.

* * * * *